United States Patent [19]

Misenko

[11] Patent Number: 5,011,689

[45] Date of Patent: Apr. 30, 1991

[54] COMPOSITION OF MATTER AND METHOD FOR TREATING POISON IVY

[75] Inventor: T. Paul Misenko, 1093 Barbe La., Bristolville, Ohio 44402

[73] Assignee: T. Paul Misenko, Bristolville, Ohio

[21] Appl. No.: 449,471

[22] Filed: Dec. 11, 1989

Related U.S. Application Data

[63] Continuation of Ser. No. 169,305, Mar. 17, 1988, abandoned.

[51] Int. Cl.$^5$ .............................................. A61K 35/78
[52] U.S. Cl. ...................... 424/195.1; 424/DIG. 13; 514/829; 514/830; 514/860; 514/862; 514/863; 514/864; 514/865
[58] Field of Search ................... 424/195.1, DIG. 13; 514/829, 830, 860, 861, 862, 863, 864, 865

[56] References Cited

PUBLICATIONS

"Home Remedies From Grandma's Pantry", C. E. Hiday, 1981, p. 12.

*Primary Examiner*—John W. Rollins
*Attorney, Agent, or Firm*—James R. Haller; Gregory P. Kaihoi; Mary P. Bauman

[57] ABSTRACT

The invention comprises a method of reducing rash formation and itching of skin caused by poison ivy. The method comprises breaking up a plant of the genus Plantago, preferably broadleaf Plantain, to release the sap therein and to form a fibrous pulp containing sap and applying an effective amount of the sap-containing pulp to the affected area of the skin.

6 Claims, No Drawings

COMPOSITION OF MATTER AND METHOD FOR TREATING POISON IVY

This application is a continuation of application Ser. No. 169,305, filed Mar. 17, 1988 now abandoned.

FIELD OF THE INVENTION

The invention relates to a method and composition of matter for reducing the inching, rash formation and redness of skin associated with an allergic response to poison ivy, poison oak and the like.

BACKGROUND OF THE INVENTION

Poison ivy, poison oak and poison sumac each has a sap that is composed of substances that provoke a sensitizing reaction in most people the first time contact with the sap occurs. After a person has become sensitized, subsequent contact with the sap produces an allergic reaction. First, the skin reddens and begins to itch. Small watery blisters appear and the inching becomes worse. Persons with poison ivy commonly scratch which slows healing and may spread the active substances from the plant's sap to other locations on the body. Boric acid solutions or calamine lotion have been used to relieve itching with only limited success.

It is fairly common for a person, when partaking in an outdoor activity, to come into contact with poison ivy and plants that cause an allergic response. Similarly, some people have an allergic response to insect bites, foods and other agents that result in the formation of itchy watery blisters like those caused by an allergic response to poison ivy. Substances that cause allergic reactions such as those described above are referred to herein as "allergens". A remedy that reduces rash formation and itching of the skin caused by these types of allergic reactions is desirable.

SUMMARY OF THE INVENTION

The invention comprises a method and composition of matter for reducing rash formation, redness and inching of skin caused by contact with poison ivy or the like. In one embodiment, the sap of a plant of the genus Plantago, preferably a plantain, is applied to an affected area of skin, the sap being carried in the fibrous portion of the plant leaves which enables the sap-containing mixture to cling to the skin.

In another embodiment the sap of a plant of the genus Plantaqo is squeezed from the leaves of the plant and applied directly to affected areas of skin or it is combined with a pharmaceutically-acceptable carrier that facilitates application of the sap to the skin.

Yet another embodiment of the invention is a composition of matter comprising sap of a plant of the enus Plantaqo or a substance derived from such sap in admixture with a pharmaceutically acceptable carrier, the sap or sap-derivative being present in a sufficient quantity to reduce rash formation and inching of skin caused by an allergic reaction.

DETAILED DESCRIPTION OF THE PREFERRED EMBODIMENT

The invention utilizes the sap of a plant of the genus Plantaqo, preferably a broadleaf plantain, to reduce rash formation, redness and itching of the skin caused by poison ivy and other allergens. Several species of the genus Plantaqo are commonly referred to as plantains. The best known species grow luxuriently as weeds in lawns and along roadsides in practically all parts of the temperate world.

Plantains are identified by basal, ribbed leaves that alternate in rosettes and that are generally elliptic or broadly ovate in shape. Several species of the Plantaqo genus distributed throughout the United States include *Plantaqo major*, (broadleaf plantain) and *Plantaqo rugelil decne*. Other names used to refer to plants of the genus *Plantaqo* include Buckhorn plantain and Blackseed plantain.

In a preferred method of the invention, the leaves of a plantain are collected and crushed to form a wet fibrous pulp containing sap of the leaves substantially evenly distributed therethrough. The fibrous portion of the leaves serves as a carrier of the sap and is capable of clinging to the skin and facilitates application. When an individual has an allergic reaction to contact with poison ivy or the like resulting in rash formation and itching, the fibrous pulp of the crushed plantain leaves is applied to the affected area. The fibrous pulp causes the mixture to cling to the affected area of the skin so that the mixture remains on the affected area of the skin for a sufficient length of time for the sap to react to reduce the itching and rash formation associated with the allergic response. The sap-containing mixture may be worn away or washed from the skin by sweating or other means during the course of the user's daily activities. Therefore, the treatment desirably is repeated twice a day or more frequently if itching begins to recur.

In another embodiment of the invention, the leaves of a plantain plant are squeezed to release the sap or juice into a container. The sap is then applied directly to the affected area of the skin. More frequent application may be necessary when the sap is applied without a carrier substance.

The sap of the plant may be combined with a pharmaceutically-acceptable carrier that will facilitate the application of the sap to the skin. A carrier is pharmaceutically-acceptable if it does not by itself cause an allergic reaction and if it does not interfere with the active properties of the sap. The sap may be mixed in a lotion, talc, jelly, oil, or any carrier that will make application to an itchy irritated area of skin easier. The composition may be applied to the skin with the fingertips, with a brush or in a spray.

One embodiment of the invention is a composition of matter comprising in admixture with a pharmaceutically-acceptable carrier, an effective amount of sap or sap-derivative from a plant of the genus Plantaqo, said amount of sap being effective to reduce or eliminate the itching and rash formation associated with poison ivy.

The invention may be used to reduce the rash formation and inching associated with various types of allergic reactions, it is not limited to reactions to poison ivy. It will reduce the itching associated with insect bites, contact dermatitis, food allergies and the like.

The invention may be more easily appreciated by reference to the following, non-limiting examples.

EXAMPLE 1

An adult male, who had a one and a half inch by four inch patch of poison ivy on his lower left rib cage was treated with the method of the invention. The affected skin had the small blisters and itching associated with an allergic reaction to poison ivy. Plant leaves of the plantain plant were broken up and the sap of the plant rubbed onto the affected area of skin. The subject reported that the itching associated with the rash formation subsided almost immediately. A second application was made 24 hours later. Within 24 hours of the first application, the blisters had subsided and appeared to be drying up. Within three days, all symptoms of the allergic response to the poison ivy were gone.

EXAMPLE II

An adult female acquired poison ivy on her midriff and abdomen. The sap of a plantain plant was applied to the affected skin. The subject reported that the inching associated with the rash was immediately relieved. The blisters dried up and disappeared within two days and the remaining redness was gone within a week.

EXAMPLE III

An adult female subject having a patch of blisters and associated inching on the top of her hand and under her chin caused by an allergic reaction to poison ivy was treated according to the invention. The sap of plantain leaves was collected and applied to the blistered and red areas of the subject's skin. The subject reported that within a minute, the inching stopped. The treatment was repeated a second time when the subject began to experience a recurrence of the itching. The subject reported that the itching again subsided immediately. The treatment was continued for about one week with applications to the affected area twice a day. In the past when the subject had acquired poison ivy it had spread swiftly over her body and that she had been unable to control the inching. When treated as described above she reported that she did not experience the itching, the poison ivy did not spread and it disappeared faster than with other remedies that she had tried.

EXAMPLE IV

The invention was used with an adult female subject that has an allergy to nuts that manifests itself in the subject in an itchy rash with small blisters similar to that caused by a reaction to poison ivy. The sap of the plantain plant was applied to the affected area as described above. The subject reported that the itching associated with the rash disappeared within 15 to 30 minutes. The treatment was repeated twice a day and to areas of itchy skin prior to outbreak of a rash. The subject reported that the area of skin affected by the rash and the itching normally associated with an outbreak of the rash and blisters were both reduced after application of the composition.

EXAMPLE V

The invention was used in a female child that has an allergic response to mosquito bites. The leaves of a plantain plant were crushed to form a green salve and the salve was applied to a mosquito bite that had begun to swell and itch. The subject reported that the itching subsided within about 15 minutes and swelling was reduced and substantially eliminated. By the next day, the bite had disappeared.

While a preferred embodiment of the present invention has been described, it should be understood that various changes, adaptations and modifications may be made therein without departing from the spirit of the invention and the scope of the appended claims.

What is claimed is:

1. A method for reducing rash formation and itching of skin caused by poison ivy comprising breaking up a plant of the genus Plantago to release the sap therein and to form a fibrous pulp containing sap and applying an effective amount of said sap-containing pulp to the affected area of skin.

2. The method of claim 1 wherein the plant is broadleaf plantain.

3. The method of claim 1 further comprising repeating application of the sap-containing pulp to the affected area until the rash and itching completely disappears.

4. A method of treating poison ivy consisting essentially of applying an effective amount of sap of a plant of the genus Plantago on the affected area of the skin.

5. The method of claim 4 wherein the plant is broadleaf plantain.

6. The method of claim 4 further comprising the step of combining the sap with a pharmaceutically acceptable carrier prior to application to the skin.

* * * * *